United States Patent
Sweeney (10) Patent No.: US 8,000,786 B2
(45) Date of Patent: *Aug. 16, 2011

(54) MULTIPLE PULSE DEFIBRILLATION FOR SUBCUTANEOUS IMPLANTABLE CARDIAC DEVICES

(75) Inventor: Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 426 days.

This patent is subject to a terminal disclaimer.

(21) Appl. No.: 12/228,327

(22) Filed: Aug. 12, 2008

(65) Prior Publication Data

US 2008/0306561 A1 Dec. 11, 2008

Related U.S. Application Data

(63) Continuation of application No. 10/985,367, filed on Nov. 9, 2004, now Pat. No. 7,418,293.

(51) Int. Cl.
*A61N 1/00* (2006.01)
(52) U.S. Cl. .......................................................... 607/5
(58) Field of Classification Search ................ 607/5, 116
See application file for complete search history.

(56) References Cited

U.S. PATENT DOCUMENTS

| | | | |
|---|---|---|---|
| 4,662,377 A | 5/1987 | Heilman et al. | |
| 4,928,688 A | 5/1990 | Mower | |
| 4,996,984 A | 3/1991 | Sweeney | |
| 5,133,353 A | 7/1992 | Hauser | |
| 5,161,528 A | 11/1992 | Sweeney | |
| 5,179,945 A | 1/1993 | Van Hofwegen et al. | |
| 5,230,337 A | 7/1993 | Dahl et al. | |
| 5,255,692 A | 10/1993 | Neubauer et al. | |
| 5,313,953 A | 5/1994 | Yomtov et al. | |
| 5,314,459 A | 5/1994 | Swanson et al. | |
| 5,318,597 A | 6/1994 | Hauck et al. | |
| 5,334,222 A | 8/1994 | Salo et al. | |
| 5,372,606 A | 12/1994 | Lang et al. | |
| 5,388,578 A | 2/1995 | Yomtov et al. | |
| 5,411,031 A | 5/1995 | Yomtov | |
| 5,411,525 A | 5/1995 | Swanson et al. | |
| 5,468,254 A | 11/1995 | Hahn et al. | |
| 5,522,853 A | 6/1996 | Kroll | |
| 5,545,186 A | 8/1996 | Olson et al. | |
| 5,620,466 A | 4/1997 | Haefner et al. | |
| 5,634,938 A | 6/1997 | Swanson et al. | |
| 5,662,688 A | 9/1997 | Haefner et al. | |
| 5,855,593 A | 1/1999 | Olson et al. | |
| 6,026,320 A | 2/2000 | Carlson et al. | |
| 6,141,581 A | 10/2000 | Olson et al. | |

(Continued)

OTHER PUBLICATIONS

Notice of Allowance dated Apr. 18, 2008 from U.S. Appl. No. 10/985,367, 7 pages.
Office Action Response dated Jan. 28, 2008 from U.S. Appl. No. 10/985,267, 12 pages.
Office Action dated Jul. 27, 2007 from U.S. Appl. No. 10/985,267, 4 pages.
Office Action Response dated May 18, 2007 from U.S. Appl. No. 10/985,267, 19 pages.

(Continued)

*Primary Examiner* — George Manuel
(74) *Attorney, Agent, or Firm* — Hollingsworth & Funk, LLC (57) ABSTRACT

Cardiac stimulation methods and systems provide for multiple pulse defibrillation, and involve sensing a fibrillation event, determining a fibrillation cycle length associated with the fibrillation event, and delivering a plurality of defibrillation pulses to treat the fibrillation event. Defibrillation pulses are delivered using a combination of subcutaneous non-intrathoracic electrodes. Delivery of each defibrillation waveform subsequent to a first defibrillation waveform is separated in time by a delay associated with the fibrillation cycle length. Delays between defibrillation waveform delivery may be associated with a percentage of the fibrillation cycle length.

27 Claims, 8 Drawing Sheets

U.S. PATENT DOCUMENTS

| | | |
|---|---|---|
| 6,221,011 B1 | 4/2001 | Bardy |
| 6,259,947 B1 | 7/2001 | Olson et al. |
| 6,270,457 B1 | 8/2001 | Bardy |
| 6,277,072 B1 | 8/2001 | Bardy |
| 6,280,380 B1 | 8/2001 | Bardy |
| 6,285,907 B1 | 9/2001 | Kramer et al. |
| 6,312,378 B1 | 11/2001 | Bardy |
| 6,336,903 B1 | 1/2002 | Bardy |
| 6,358,203 B2 | 3/2002 | Bardy |
| 6,368,284 B1 | 4/2002 | Bardy |
| 6,371,922 B1 | 4/2002 | Baumann et al. |
| 6,398,728 B1 | 6/2002 | Bardy |
| 6,411,848 B2 | 6/2002 | Kramer et al. |
| 6,424,865 B1 | 7/2002 | Ding |
| 6,440,066 B1 | 8/2002 | Bardy |
| 6,459,929 B1 | 10/2002 | Hopper et al. |
| 6,487,443 B2 | 11/2002 | Olson et al. |
| 6,542,775 B2 | 4/2003 | Ding et al. |
| 6,597,951 B2 | 7/2003 | Kramer et al. |
| 7,349,742 B2 * | 3/2008 | Heil et al. .................. 607/116 |
| 2004/0215240 A1 | 10/2004 | Lovett et al. |
| 2004/0230249 A1 | 11/2004 | Haefner |
| 2006/0095083 A1 | 5/2006 | Zhang et al. |
| 2006/0100670 A1 | 5/2006 | Sweeney |

OTHER PUBLICATIONS

Office Action dated Feb. 13, 2007 from U.S. Appl. No. 10/985,267, 5 pages.

Office Action Response dated Nov. 3, 2006 from U.S. Appl. No. 10/985,267, 12 pages.

Office Action dated Jun. 30, 2006 from U.S. Appl. No. 10/985,267, 10 pages.

1999, McDaniel et al. Double pulse transthoracic defibrillation in the calf using percent fibrillation cycle length as spacing determinate. *Pacing and Electrophysiology*. 1999, vol. 22:1440-1447. Abstract Only.

1995, Sweeney et al. Characteristics of multiple-shock defibrillation. *Journal of Cardiovascular Electrophysiology*. 1995; vol. 6:89-102. Abstract Only.

1994, Sweeney et al. Double-pulse defibrillation using pulse separation based on the fibrillation cycle length. *Journal of Cardiovascular Electrophysiology*. 1994; vol. 5:761-770. Abstract Only.

* cited by examiner

MULTIPLE PULSE DEFIBRILLATION FOR SUBCUTANEOUS IMPLANTABLE CARDIAC DEVICES

RELATED APPLICATIONS

This application is a continuation of U.S. patent application Ser. No. 10/985,367, filed on Nov. 9, 2004, to issue as U.S. Pat. No. 7,418,293 on Aug. 26, 2008, which is hereby incorporated herein by reference.

FIELD OF THE INVENTION

The present invention relates generally to implantable medical devices and, more particularly, to subcutaneous cardiac sensing and stimulation devices employing delivery of multiple electrical defibrillation pulses with timing based on the sensed cardiac activity.

BACKGROUND OF THE INVENTION

The healthy heart produces regular, synchronized contractions. Rhythmic contractions of the heart are normally initiated by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and may be a potential life-threatening event. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid contractions of the atria. Besides being hemodynamically inefficient, the rapid contractions of the atria may also adversely affect the ventricular rate.

Ventricular tachycardia occurs, for example, when electrical activity arises in the ventricular myocardium at a rate more rapid than the normal sinus rhythm. Ventricular tachycardia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

Typical implantable cardioverter/defibrillators include one or more endocardial leads to which at least one defibrillation electrode is connected. Such implantable cardioverter/defibrillators are capable of delivering high-energy shocks to the heart, interrupting the ventricular tachyarrhythmia or ventricular fibrillation, and allowing the heart to resume normal sinus rhythm.

SUMMARY OF THE INVENTION

The present invention is directed to cardiac stimulation methods and systems that provide for multiple pulse defibrillation. A method of delivering a subcutaneous defibrillation therapy in accordance with the present invention involves sensing a fibrillation event, determining a fibrillation cycle length associated with the fibrillation event, and delivering two or more defibrillation pulses to treat the fibrillation event. Delivery of each pulse subsequent to the first pulse is separated in time by a delay associated with the fibrillation cycle length.

Embodiments of the present invention deliver the defibrillation pulses from one or more subcutaneous non-intrathoracic electrode arrangements. Multiple defibrillation pulses may be delivered following a delay associated with a percentage of the fibrillation cycle length. The delay may be a fixed percentage of the cycle length, or may be a variable percentage of the cycle length. Three or more defibrillation pulses may be delivered with fixed or variable delays, one or more of which may be associated with a percentage of the fibrillation cycle length.

Delivery of the defibrillation pulses may be facilitated using the same or different electrode arrangements/combination of electrodes. Sensing defibrillation events may be facilitated using the same or different electrode arrangements/combination of electrodes. Embodiments of the present invention may provide for delays between defibrillation pulses greater than about 50 percent of the fibrillation cycle length, greater than about 75 percent of the fibrillation cycle length, and between about 75 to 100 percent of the fibrillation cycle length, respectively. The fibrillation cycle length may be determined using various techniques, including a Fourier analysis of the fibrillation event, an auto-correlation analysis of the fibrillation event, and/or by counting signal features of the fibrillation event over a duration of time.

Defibrillation pulses may be substantially similar in terms of one or more of amplitude, duration, and phase, or may be substantially different in terms of one or more of amplitude, duration, and phase. Defibrillation pulses may include monophasic pulses, biphasic pulses, or a combination of monophasic and biphasic pulses.

A system for delivering a subcutaneous defibrillation therapy in accordance with the present invention includes a housing configured for subcutaneous non-intrathoracic placement relative to a patient's heart. Detection circuitry may be provided in the housing, the detection circuitry configured to detect a fibrillation event. Energy delivery circuitry may also be provided in the housing, and coupled to one or more electrode arrangements configured for subcutaneous non-intrathoracic placement relative to the patient's heart. A controller may further be provided in the housing and coupled to the detection and energy delivery circuitry, the controller configured to determine a fibrillation cycle length associated with the fibrillation event. The controller may coordinate delivery of defibrillation pulses using a delay between pulses associated with a fixed or variable percentage of the fibrillation cycle length.

The controller may be further configured to deliver three or more pulses in a multiple pulse defibrillation waveform, where the pulses may be separated by delays of the same or differing lengths. One or more of the delays may be associated with a percentage of the fibrillation cycle length. One or more electrode arrangements/electrode combinations may be used for detection of the fibrillation event and delivery of the defibrillation pulses. For example, a first electrode arrangement or combination may be used for detection of the fibrillation event and a second electrode arrangement or combination may be used for delivery of the defibrillation pulses. Other embodiments include a first electrode arrangement/combination used for delivery of an initial pulse and a second electrode arrangement/combination used for delivery of one or more subsequent pulses. Any combination of electrodes may be used for delivery of any of the multiple defibrillation pulses without departing from the scope of the present invention.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device according to the present invention may include one or more of the features, structures, methods, or combinations thereof described hereinbelow. For example, a cardiac stimulator may be implemented to include one or more of the advantageous features and/or processes described below. It is intended that such a stimulator, or other implanted or partially implanted device need not include all of the features described herein, but may be implemented to include selected features that provide for useful structures and/or functionality. Such a device may be implemented to provide a variety of functions.

A wide variety of implantable cardiac stimulation devices may be configured to implement a multiple pulse defibrillation methodology of the present invention. A non-limiting, representative list of such devices includes defibrillators, cardioverters, resynchronizers, and other cardiac therapy delivery devices. These devices may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). In general, however, a multiple pulse defibrillation methodology of the present invention is preferably implemented using subcutaneous, non-intrathoracic electrodes. Embodiments of the present invention are referred to herein generally as patient-internal medical devices (PIMD) for convenience. A PIMD implemented in accordance with the present invention may incorporate one or more of the electrode types identified above and/or combinations thereof.

Figure 1:
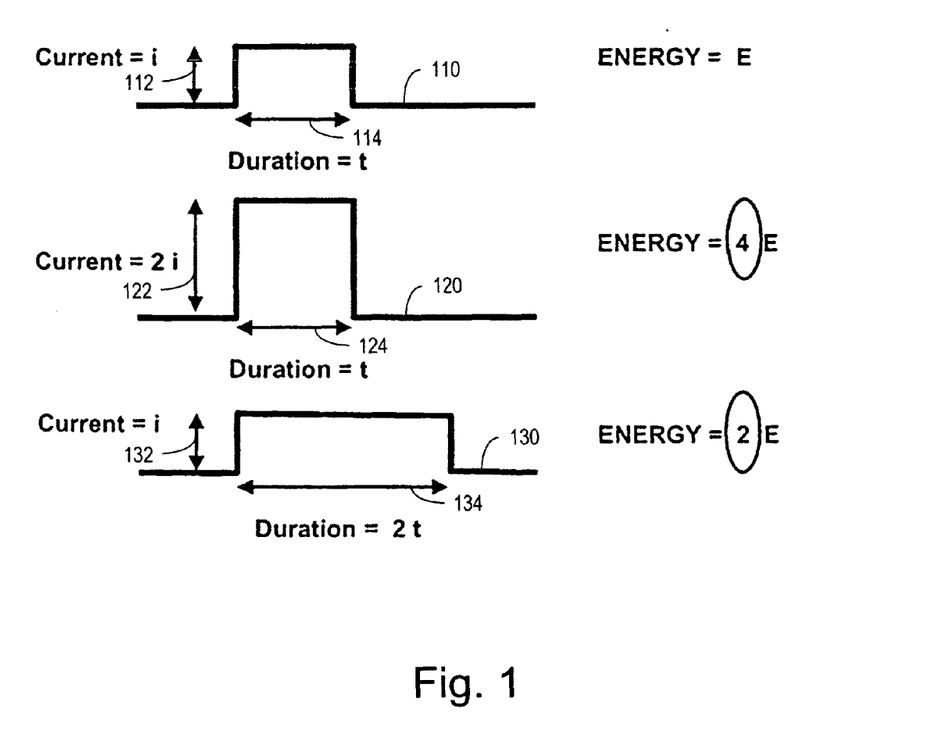
FIG. 1 is a graph of three pulses of differing energies that may be used to describe cardiac defibrillation levels.

FIG. 1 is a graph of three pulses that may be used to describe cardiac defibrillation energies. The ordinate of the graph illustrated in FIG. 1 is time, and the abscissa is current amplitude, indicative of the current delivered by a cardiac defibrillator. A plot 110 illustrates a normalized square pulse at a current 112 and a duration 114. The energy associated with the plot 110 is designated E. A plot 120 is illustrated as having a current amplitude 122 twice that of the current amplitude 112 of plot 110, but having a duration 124, which is the same as duration 114 of plot 110. Due to the square law for energy, the energy of the pulse of plot 120 is four times the energy of the pulse in plot 110, or 4E. A plot 130 is illustrated as having a current amplitude 132, which is the same as that of the current amplitude 112 of plot 110, but at a duration 134 that is twice the duration 114 of plot 110. The energy of the pulse of plot 130 is only twice that of the pulse in plot 110 (2E), since the energy square law does not apply in this case. In applications where energy is potentially limited, such as for implantable devices using batteries for power, pulses of longer duration are more efficient than pulses of larger current, assuming the desired therapy objective may be achieved using either pulse type.

Figure 2:
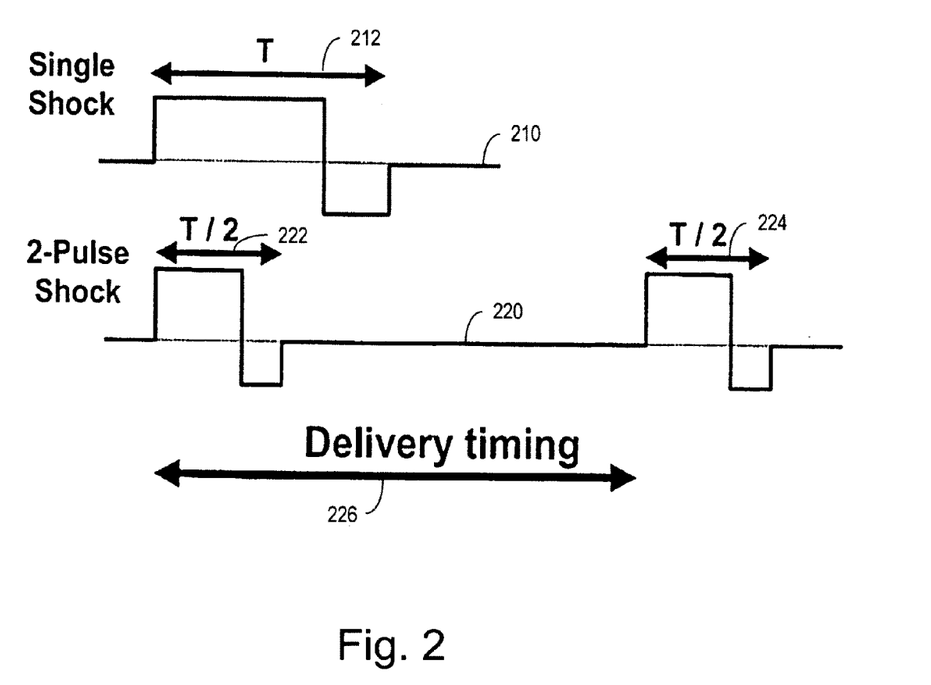
FIG. 2 is a graph of three pulses of differing durations that may be used to describe cardiac defibrillation timing.

FIG. 2 is a graph of three pulses of differing durations that may be used to describe cardiac defibrillation timing. The ordinate of the graph illustrated in FIG. 2 is time, and the abscissa is current amplitude, indicative of the current delivered by a cardiac defibrillator. A plot 210 illustrates a bipolar pulse having a period 212 designated by T. In accordance with the present invention, it is possible to achieve defibrillation, at similar energy, by splitting a pulse of period 212 into two pulses of shorter period (e.g., T/2), separated by a delay in delivery timing 226. For example, a 2-pulse signal 220 is separated by delivery timing delay 226. Each of a pulse 222 and a pulse 224 has a period of T/2, thereby maintaining similar energies, such that the pulse of plot 210 has an energy approximately equal to that of the multiple pulse of 2-pulse signal 220. The example of splitting the 2-pulse signal 220 into T/2 durations at similar current amplitudes is for illustrative purposes only, and not for purposes of limitation.

Figure 3:
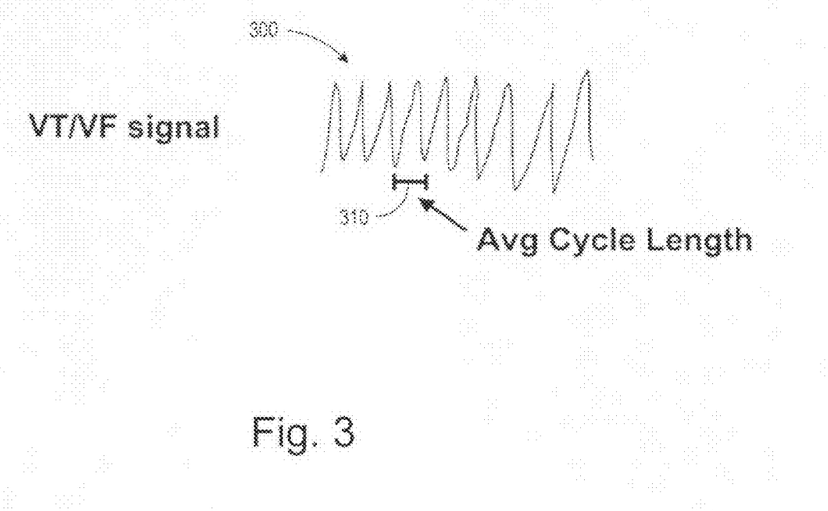
FIG. 3 is an illustration depicting the average cycle length of a cardiac ventricular tachycardia and/or ventricular fibrillation episode.

The delivery timing 226 plays an important role in the efficacy of defibrillation for use in multiple pulse defibrillation systems and methods. Referring now to FIG. 3, a graph 300 depicts an average cycle length 310 associated with a cardiac ventricular tachycardia and/or ventricular fibrillation episode. The signal of graph 300 may be acquired using a cardiac electrode arrangement to measure the electrophysiological signals produced by a patient's heart during a ventricular tachycardia and/or ventricular fibrillation episode. By determining the period of oscillation of the ventricular tachycardia and/or ventricular fibrillation episode, the average cycle length 310 may be defined. For example, zero crossings may be determined for the signal 300, and used to determine the average cycle length 310. Other methods for determining average cycle length include, for example, auto-correlation techniques, Fourier transform methods, and counting other morphological features, such as maximas, minimas, inflection points, or other features.

Figure 4:
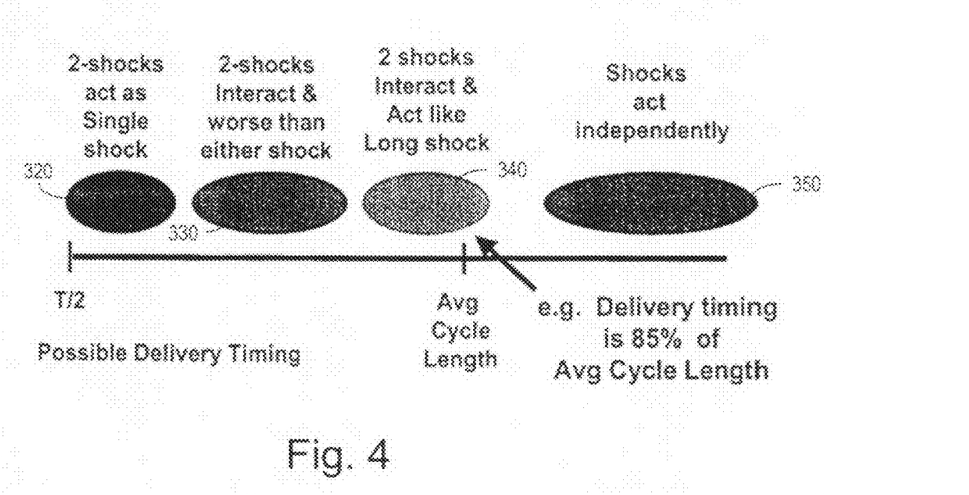
FIG. 4 is a graph depicting regions of separation and interaction for multiple pulse defibrillation therapy in accordance with the present invention.

Delivering multiple defibrillation pulses separated by a delay in delivery timing relative to the average cycle length of the ventricular tachycardia and/or ventricular fibrillation provides defibrillation efficacy at a defibrillation energy similar to that of a single pulse. FIG. 4 is a graph depicting regions of separation and interaction for multiple pulse defibrillation in accordance with the present invention.

A region 320 exists at about a delivery delay up to about 35% of the average cycle length. The region 320 is considered to be the region where the delay between the multiple pulses is so short relative to a single pulse, that the cardiac response to the delay is imperceptible.

A region 330 exists at a delivery delay from about 35% to about 50% of the average cycle length, wherein the cardiac response to the separated pulses is less efficacious than a single pulse. The region 330 may be considered as a region where destructive interference occurs between the cardiac response to the first pulse and the cardiac response to a subsequent pulse. Because of the region 330, delays greater than about 50% of the average cycle length may provide improved efficacy for multiple pulse defibrillation.

A region 350 exists at delay times greater than about 125% of the average cycle length, where the pulses act independently. Since multiple pulses are delivered with each pulse occurring during a separate fibrillation cycle, significant interactions are not obtained, and improvements in efficacy are not observed. In view of the region 350, delays less than about 125% of the average cycle length may provide improved efficacy for multiple pulse defibrillation.

However, there exists a region 340, at a multiple pulse timing delay between about 50% and about 125%, and typically between about 75% and about 100% of the average cycle length, where the cardiac response to multiple separated pulses is similar to the cardiac response to a single pulse. This region, which may be considered similar to a region of constructive interference for the cardiac response to the separated pulses, provides opportunity for improved efficacy of defibrillation, decreased energy requirements for defibrillation systems, or both improved efficacy and decreased energy.

For example, a single pulse at current I and duration T may be replaced with two pulses at current I and duration T/2, separated by a delay of 85% of the average cycle length. This multiple pulse defibrillation therapy may have similar or better cardiac response than the single pulse, but save $\frac{1}{3}^{rd}$ the energy. By way of further example, a single pulse at current I and duration T (=24 milliseconds) may be replaced with two pulses at current 0.81×I and duration T/2 (=12 milliseconds), separated by a delay of 85% of the average cycle length. The multiple pulse defibrillation at a decreased current and an increased duration may provide a significantly better cardiac response than a single pulse using the same energy. As will now be appreciated by those skilled in the art, energy may be advantageously adjusted, such as by selecting a number of pulses, pulse widths, and amplitudes, to provide a desired level of defibrillation efficacy and energy conservation in accordance with the present invention.

Figure 5:
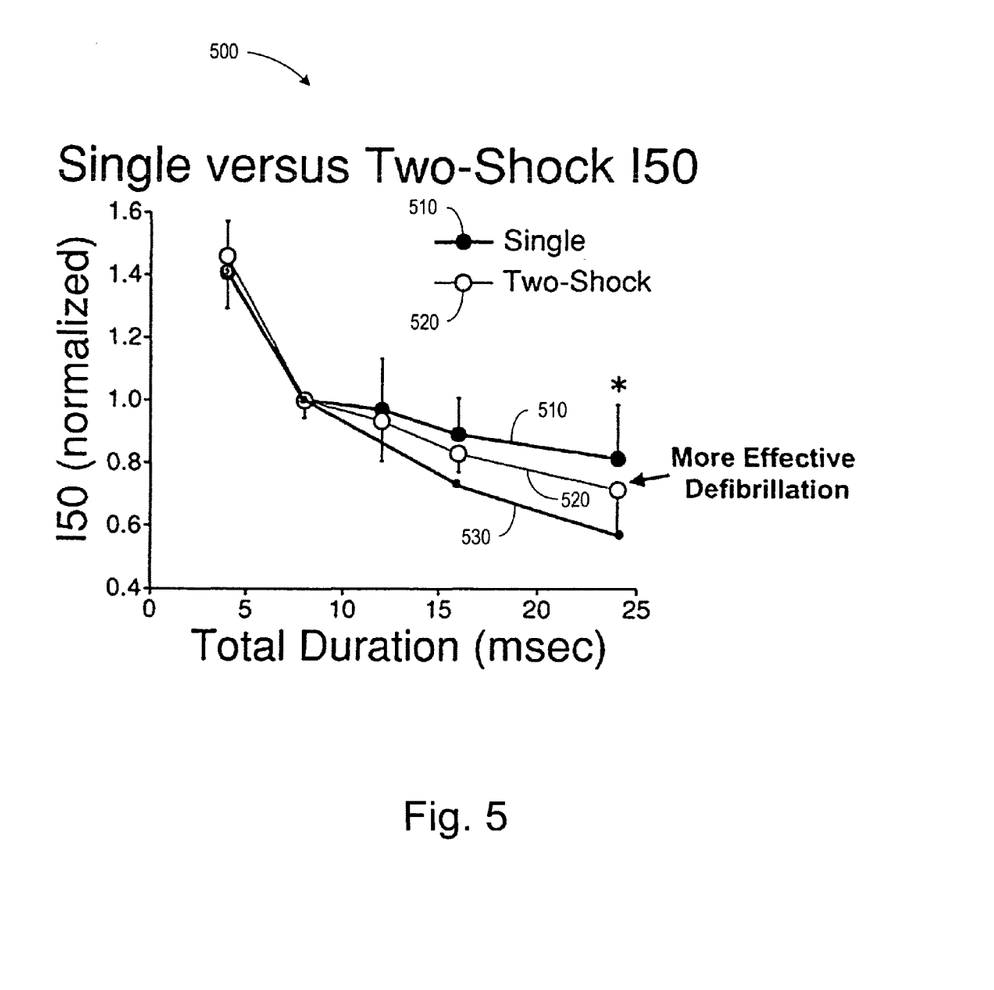
FIG. 5 is a graph of energy delivery versus defibrillation shock duration developed from single shock and two shock multiple pulse defibrillation studies performed in accordance with the present invention.

In order to illustrate advantages of multiple pulse defibrillation methods of the present invention, preclinical studies were performed on canine subjects. FIG. 5 is a graph 500 comparing single shock control group and two shock multiple pulse defibrillation group preclinical studies performed in accordance with the present invention. The ordinate of the graph illustrated in FIG. 5 is the total duration of defibrillation shock, and the abscissa is normalized (I50) current, indicative of the current delivered by a cardiac defibrillator necessary to defibrillate 50 percent of the test subjects.

The graph 500 includes defibrillation measures in the same canine subjects with a single shock control 510, and a two shock multiple pulse defibrillation 520. Graph 500 also includes an estimation plot 530 of the (I50) current necessary to achieve equal energy as the single shock control group 510. The multiple pulse defibrillation 520 exhibited more effective defibrillation at less current than the control 510 particularly at longer total shock durations. Graph 500 demonstrates that a multiple pulse defibrillation methodology in accordance with the present invention provides an opportunity for a 20% decrease in defibrillation current to achieve similar results to the control group in a PIMD.

The ability to defibrillate more effectively using multiple pulse defibrillation in accordance with the present invention permits defibrillation with longer shock durations and lower shock currents. This is particularly useful for subcutaneous implantable cardiac devices where shock electrodes are not situated near, or in direct contact, with the cardiac tissue. In such electrode configurations, the shock current from the defibrillation electrodes must distribute throughout the entire thorax so that only a relatively small fraction of that current passes directly through the cardiac tissue to achieve defibrillation.

For instance, say that a subcutaneous single shock with a 12-milliseconds duration delivered a current (Ic) to the cardiac tissue. To achieve this current in the cardiac tissue, a current of (F×I) must be applied to the subcutaneous defibrillation electrodes where (1/F) is the fraction of that applied current that passes directly through the cardiac tissue for defibrillation. Now, if successful defibrillation required that the cardiac tissue current be (Id) for a single 12-milliseconds shock, then the current at the subcutaneous electrodes would need to be increased to (F×I×Id/Ic) and the energy would need to be increased by a factor of $(Id^2/Ic^2)$. On the other hand, doubling the total shock duration to 24 milliseconds by multiple pulse defibrillation in accordance with the present invention, would permit successful defibrillation with an applied current of (F×I×0.74×Id/Ic) and the energy would be increased by a factor of $(0.54 \times Id^2/Ic^2)$. Thus, compared to increasing the intensity of a single shock to achieve subcutaneous defibrillation, doubling its total duration by multiple pulse defibrillation in accordance with the present invention will reduce the required defibrillation energy by a factor of (0.54) while at the same time reducing the required current by a factor of 0.74. In cases where F is on the order of 5 to 10, such as in subcutaneous defibrillation, this is particularly important since it limits the maximum current required of the subcutaneous defibrillator.

For purposes of illustration, and not of limitation, various embodiments of devices that may implement multiple pulse defibrillation in accordance with the present invention are described herein in the context of PIMDs that may be implanted under the skin in the chest region of a patient. A PIMD may, for example, be implanted subcutaneously such that all or selected elements of the device are positioned on the patient's front, back, side, or other body locations suitable for sensing cardiac activity and/or delivering cardiac stimulation therapy. It is understood that elements of the PIMD may be located at several different body locations, such as in the chest, abdominal, or subclavian region with electrode elements respectively positioned at different regions near, around, in, or on the heart.

The primary housing (e.g., the active or non-active can) of the PIMD, for example, may be configured for positioning outside of the rib cage at an intercostal or subcostal location, within the abdomen, or in the upper chest region (e.g., subclavian location, such as above the third rib). In one implementation, one or more leads incorporating electrodes may be located in direct contact with the heart, great vessels or coronary vasculature, such as via one or more leads implanted by use of conventional transvenous delivery approaches. In another implementation, one or more electrodes may be located on the primary housing and/or at other locations about, but not in direct contact with the heart, great vessel, or coronary vasculature.

In a further implementation, for example, one or more electrode subsystems or electrode arrays may be used to sense cardiac activity and deliver cardiac stimulation energy in a PIMD configuration employing an active can or a configuration employing a non-active can. Electrodes may be situated at anterior and/or posterior locations relative to the heart. Examples of useful electrode locations and features that may be incorporated in various embodiments of the present invention are described in commonly owned, co-pending U.S. Publication Nos. 2004/0230230; 2004/0215240; 2005/0004615; and 2004/0230229; and U.S. Pat. Nos. 7,299,086 and 7,499,750, which are hereby incorporated herein by reference.

Certain configurations illustrated herein are generally described as capable of implementing various functions traditionally performed by an implantable cardioverter/defibrillator (ICD), and may operate in numerous cardioversion/defibrillation modes as are known in the art. Examples of ICD circuitry, structures, and functionality, aspects of which may be incorporated in a PIMD of a type that may benefit from multiple pulse defibrillation methods and implementations are disclosed in commonly owned U.S. Pat. Nos. 4,996,984; 5,133,353; 5,161,528; 5,179,945; 5,314,459; 5,318,597; 5,620,466; and 5,662,688, which are hereby incorporated herein by reference.

A PIMD in accordance with the present invention may implement diagnostic and/or monitoring functions as well as provide cardiac stimulation therapy. Examples of cardiac monitoring circuitry, structures, and functionality, aspects of which may be incorporated in a PIMD of a type that may benefit from multiple pulse defibrillation methods and implementations are disclosed in commonly owned U.S. Pat. Nos. 5,313,953; 5,388,578; and 5,411,031, which are hereby incorporated herein by reference.

Various embodiments described herein may be used in connection with congestive heart failure (CHF) monitoring, diagnosis, and/or therapy. A PIMD of the present invention may incorporate CHF features involving dual-chamber or bi-ventricular pacing/therapy, cardiac resynchronization therapy, cardiac function optimization, or other CHF related methodologies. For example, any PIMD of the present invention may incorporate features of one or more of the following references: commonly owned U.S. Pat. Nos. 6,411,848; 6,285,907; 4,928,688; 6,459,929; 5,334,222; 6,026,320; 6,371,922; 6,597,951; 6,424,865; 6,542,775 and 7,260,432, each of which is hereby incorporated herein by reference.

A PIMD may be used to implement various diagnostic functions, which may involve performing rate-based, pattern and rate-based, and/or morphological tachyarrhythmia discrimination analyses. Subcutaneous, cutaneous, and/or external sensors may be employed to acquire physiologic and non-physiologic information for purposes of enhancing tachyarrhythmia detection and termination. It is understood that configurations, features, and combination of features described in the present disclosure may be implemented in a wide range of implantable medical devices, and that such embodiments and features are not limited to the particular devices described herein.

Figure 6:
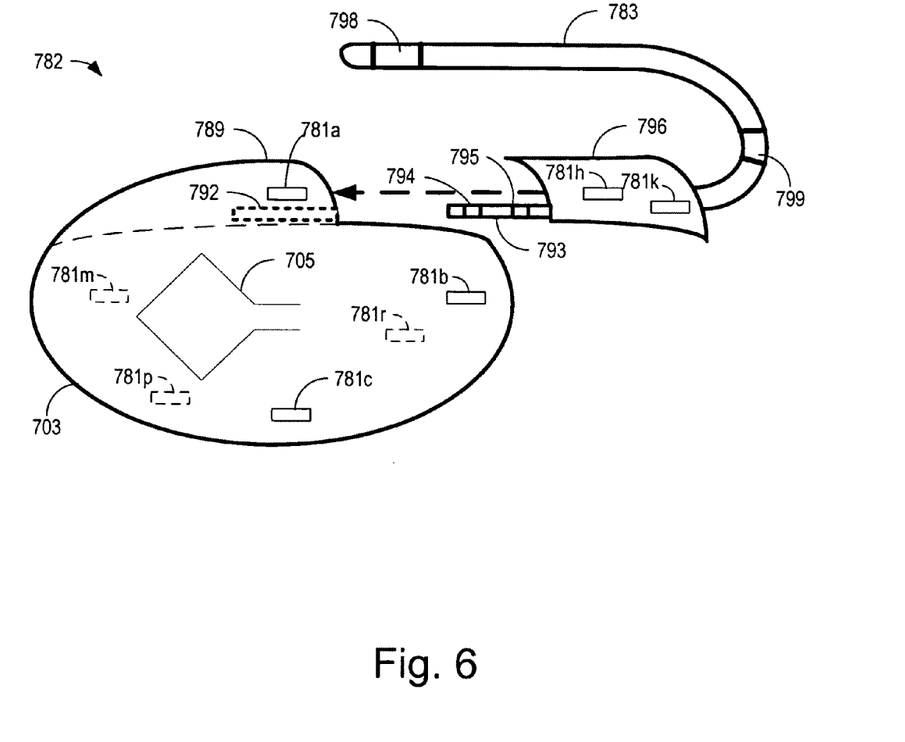
FIG. 6 is a top view of an implantable cardiac device in accordance with the present invention, including an antenna electrode and a lead/header arrangement.

FIG. 6 is a top view of a PIMD 782 in accordance with the present invention, having at least two electrodes. One electrode is illustrated as an antenna 705 of the PIMD that may also be used for RF communications. The PIMD 782 shown in the embodiment illustrated in FIG. 6 includes a first electrode 798 and a second electrode 799 coupled to a can 703 through a header 789, via an electrode module 796. The first electrode 798 and second electrode 799 may be located on a lead 783 (single or multiple lead, or electrode array), or may be located directly in or on the electrode module 796.

The can 703 is illustrated as incorporating the header 789. The header 789 may be configured to facilitate removable attachment between an electrode module 796 and the can 703, as is shown in the embodiment depicted in FIG. 6. The header 789 includes a female coupler 792 configured to accept a male coupler 793 from the electrode module 796. The male coupler 793 is shown having two electrode contacts 794, 795 for coupling one or more electrodes 798, 799 through the electrode module 796 to the can 703. An electrode 781*h* and an electrode 781*k* are illustrated on the header 789 of the can 703 and may also be coupled through the electrode module 796 to the can 703. The can 703 may alternatively, or in addition to the header electrodes 781*h*, 781*k* and/or first and second electrodes 798, 799, include one or more can electrodes 781*a*, 781*b*, 781*c*.

Electrodes may also be provided on the back of the can 703, typically the side facing externally relative to the patient after implantation. For example, electrodes 781*m*, 781*p*, and 781*r* are illustrated as positioned in or on the back of the can 703. Providing electrodes on both front and back surfaces of the can 703 provides for a three-dimensional spatial distribution of the electrodes, which may provide additional discrimination capabilities. Further description of three-dimensional configurations are described in U.S. Publication No. 2005/0197674, previously incorporated by reference.

In this and other configurations, the header 789 incorporates interface features (e.g., electrical connectors, ports, engagement features, and the like) that facilitate electrical connectivity with one or more lead and/or sensor systems, lead and/or sensor modules, and electrodes. The header 789 may also incorporate one or more electrodes in addition to, or instead of, the electrodes provided by the lead 783, such as electrodes 781*h* and 781*k*, to provide more available vectors to the PIMD. The interface features of the header 789 may be protected from body fluids using known techniques.

The PIMD 782 may further include one or more sensors in or on the can 703, header 789, electrode module 796, or lead(s) that couple to the header 789 or electrode module 796. Useful sensors may include electrophysiologic and non-electrophysiologic sensors, such as an acoustic sensor, an impedance sensor, a blood sensor, such as an oxygen saturation sensor (oximeter or plethysmographic sensor), a blood pressure sensor, minute ventilation sensor, or other sensor described or incorporated herein.

Figure 7:
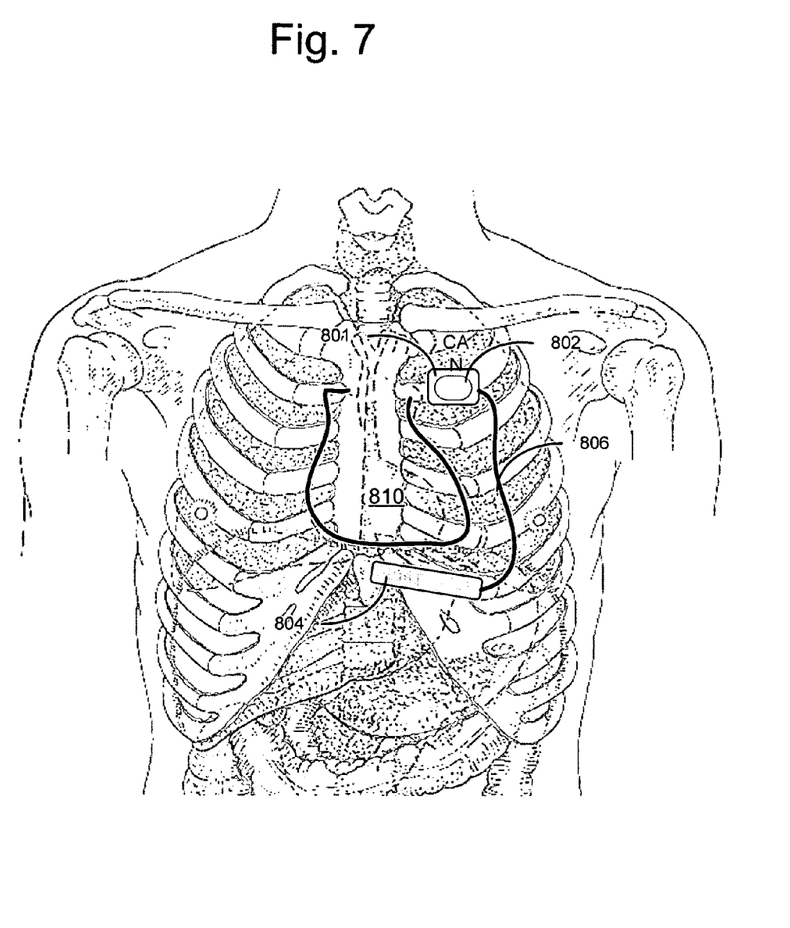
FIG. 7 is a diagram illustrating components of a cardiac stimulation device including an electrode array in accordance with an embodiment of the present invention.

In one configuration, as is illustrated in FIG. 7, electrode subsystems of a PIMD system are arranged about a patient's heart 810. The PIMD system includes a first electrode subsystem, including a can electrode 802, and a second electrode subsystem 804 that includes at least two electrodes or at least one multi-element electrode. The second electrode subsystem 804 may include a number of electrodes used for sensing and/or electrical stimulation.

In various configurations, the second electrode subsystem 804 may include a combination of electrodes. The combination of electrodes of the second electrode subsystem 804 may include coil electrodes, tip electrodes, ring electrodes, multi-element coils, spiral coils, spiral coils mounted on non-conductive backing, screen patch electrodes, subcutaneous arrays, and other electrode configurations. A suitable non-conductive backing material is silicone rubber, for example.

The can electrode 802 is positioned on the housing 801 that encloses the PIMD electronics. In one embodiment, the can electrode 802 includes the entirety of the external surface of the housing 801. In other embodiments, various portions of the housing 801 may be electrically isolated from the can electrode 802 or from tissue. For example, the active area of the can electrode 802 may include all or a portion of either the anterior or posterior surface of the housing 801 to direct current flow in a manner advantageous for cardiac sensing and/or stimulation.

Portions of the housing may be electrically isolated from tissue to optimally direct current flow. For example, portions of the housing 801 may be covered with a non-conductive, or otherwise electrically resistive, material to direct current flow. Suitable non-conductive material coatings include those formed from silicone rubber, polyurethane, or parylene, for example.

Figure 8:
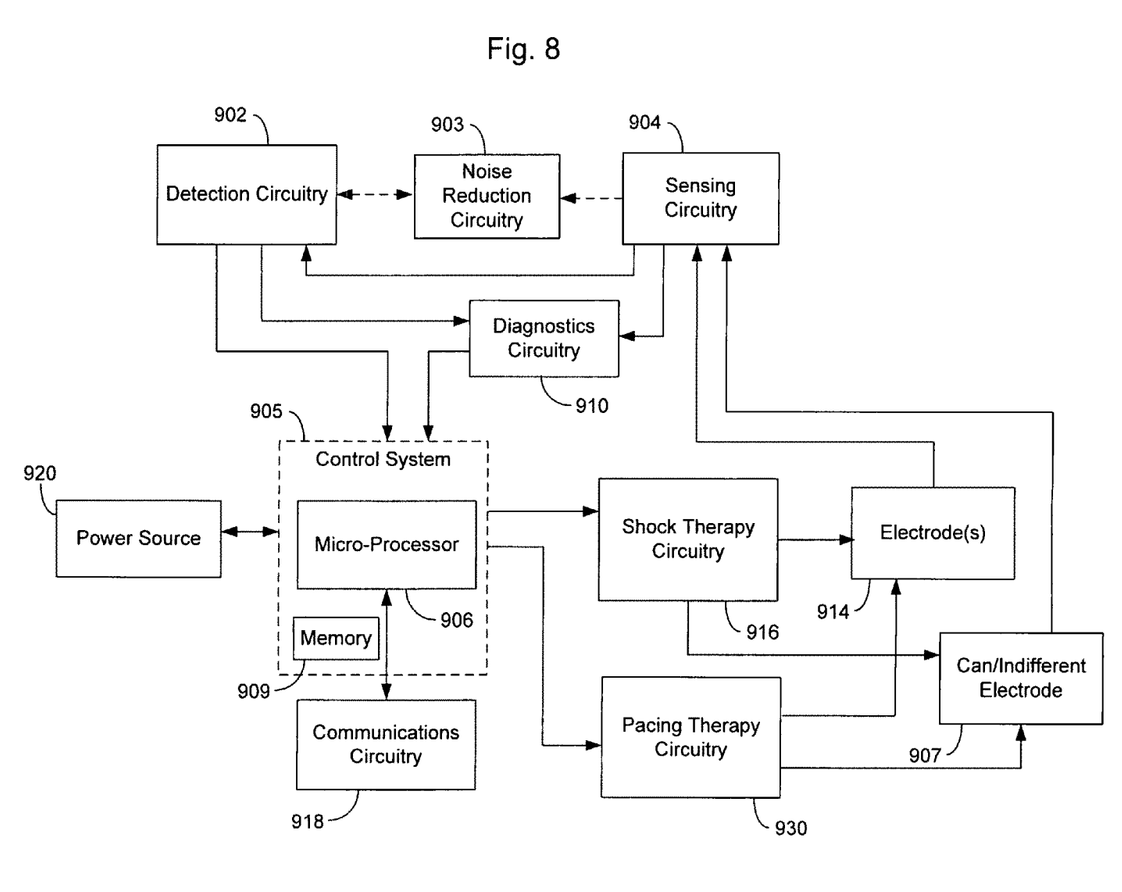
FIG. 8 is a block diagram illustrating various components of a cardiac stimulation device in accordance with an embodiment of the present invention.

FIG. 8 is a block diagram depicting various componentry of different arrangements of a PIMD in accordance with embodiments of the present invention. The components, functionality, and configurations depicted in FIG. 8 are intended to provide an understanding of various features and combinations of features that may be incorporated in a PIMD. It is understood that a wide variety of device configurations are contemplated, ranging from relatively sophisticated to relatively simple designs. As such, particular PIMD configurations may include some componentry illustrated in FIG. 8, while excluding other componentry illustrated in FIG. 8.

Illustrated in FIG. 8 is a processor-based control system 905, which includes a micro-processor 906 coupled to appropriate memory (volatile and/or non-volatile) 909, it being understood that any logic-based control architecture may be used. The control system 905 is coupled to circuitry and components to sense, detect, and analyze electrical signals produced by the heart and deliver electrical stimulation energy to the heart under predetermined conditions to treat cardiac arrhythmias. The control system 905 and associated components also provide pacing therapy to the heart. The electrical energy delivered by the PIMD may be in the form of low energy pacing pulses or high-energy pulses for cardioversion or defibrillation.

Cardiac signals are sensed using the electrode(s) 914 and the can or indifferent electrode 907 provided on the PIMD housing. Cardiac signals may also be sensed using only the electrode(s) 914, such as in a non-active can configuration. As such, unipolar, bipolar, or combined unipolar/bipolar electrode configurations as well as multi-element electrodes, subcutaneous arrays, and combinations of noise canceling and standard electrodes may be employed. The sensed cardiac signals are received by sensing circuitry 904, which includes sense amplification circuitry and may also include filtering circuitry and an analog-to-digital (A/D) converter. The sensed cardiac signals processed by the sensing circuitry 904 may be received by noise reduction circuitry 903, which may further reduce noise before signals are sent to the detection circuitry 902.

Detection circuitry 902 may include a signal processor that coordinates analysis of the sensed cardiac signals and/or other sensor inputs to detect cardiac arrhythmias, such as, in particular, tachyarrhythmia. Rate based and/or morphological discrimination algorithms may be implemented by the signal processor of the detection circuitry 902 to detect and verify the presence and severity of an arrhythmic episode.

The detection circuitry 902 communicates cardiac signal information to the control system 905. Memory circuitry 909 of the control system 905 contains parameters for operating in various sensing, defibrillation, and, if applicable, pacing modes, and stores data indicative of cardiac signals received by the detection circuitry 902. The memory circuitry 909 may also be configured to store historical ECG and therapy data, which may be used for various purposes and transmitted to an external receiving device as needed or desired.

In certain configurations, the PIMD may include diagnostics circuitry 910. The diagnostics circuitry 910 typically receives input signals from the detection circuitry 902 and the sensing circuitry 904. The diagnostics circuitry 910 provides diagnostics data to the control system 905, it being understood that the control system 905 may incorporate all or part of the diagnostics circuitry 910 or its functionality. The control system 905 may store and use information provided by the diagnostics circuitry 910 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

The control system 905 processes cardiac signal data received from the detection circuitry 902 and initiates appropriate tachyarrhythmia therapies to terminate cardiac arrhythmic episodes and return the heart to normal sinus rhythm. The control system 905 is coupled to shock therapy circuitry 916. The shock therapy circuitry 916 is coupled to the electrode(s) 914 and the can or indifferent electrode 907 of the PIMD housing.

Upon command, the shock therapy circuitry 916 delivers multiple pulse defibrillation stimulation energy to the heart in accordance with the present invention. In a more sophisticated configuration, the shock therapy circuitry 916 is controlled to deliver defibrillation therapies and cardioversion therapies. Examples of PIMD high energy delivery circuitry, structures and functionality, aspects of which may be incorporated in a PIMD of a type that may benefit from aspects of the present invention are disclosed in commonly owned U.S. Pat. Nos. 5,372,606; 5,411,525; 5,468,254; and 5,634,938, which are hereby incorporated herein by reference.

Arrhythmic episodes may also be detected and verified by morphology-based analysis of sensed cardiac signals as is known in the art. Tiered or parallel arrhythmia discrimination algorithms may also be implemented using both rate-based and morphologic-based approaches. Further, a rate and pattern-based arrhythmia detection and discrimination approach may be employed to detect and/or verify arrhythmic episodes, such as the approach disclosed in U.S. Pat. Nos. 6,487,443; 6,259,947; 6,141,581; 5,855,593; and 5,545,186, which are hereby incorporated herein by reference.

In accordance with another configuration, a PIMD may incorporate a cardiac pacing capability in addition to multiple pulse defibrillation capabilities. As is shown in FIG. 8, the PIMD includes pacing therapy circuitry 930 that is coupled to the control system 905 and the electrode(s) 914 and can/indifferent electrodes 907. Upon command, the pacing therapy circuitry 930 delivers pacing pulses to the heart in accordance with a selected pacing therapy.

The PIMD shown in FIG. 8 may be configured to receive signals from one or more physiologic and/or non-physiologic sensors. Depending on the type of sensor employed, signals generated by the sensors may be communicated to transducer circuitry coupled directly to the detection circuitry 902 or indirectly via the sensing circuitry 904. It is noted that certain sensors may transmit sense data to the control system 905 without processing by the detection circuitry 902.

Communications circuitry 918 is coupled to the microprocessor 906 of the control system 905. The communications circuitry 918 allows the PIMD to communicate with one or more receiving devices or systems situated external to the PIMD. It is noted that physiologic or non-physiologic sensors equipped with wireless transmitters or transceivers may communicate with a receiving system external of the patient.

The communications circuitry 918 allows the PIMD to communicate with an external programmer. In one configuration, the communications circuitry 918 and the programmer unit (not shown) use a wire loop antenna and a radio frequency telemetric link, as is known in the art, to receive and transmit signals and data between the programmer unit and communications circuitry 918. In this manner, programming commands and data are transferred between the PIMD and the programmer unit during and after implant. Using a programmer, a physician is able to set or modify various parameters used by the PIMD. For example, a physician may set or modify parameters affecting sensing, detection, pacing, and defibrillation functions of the PIMD, including pacing and cardioversion/defibrillation therapy modes.

Typically, the PIMD is encased and hermetically sealed in a housing suitable for implanting in a human body as is known in the art. Power to the PIMD is supplied by an electrochemical power source 920 housed within the PIMD.

The detection circuitry 902, which is coupled to a microprocessor 906, may be configured to incorporate, or communicate with, specialized circuitry for processing sensed cardiac signals in manners particularly useful in a cardiac sensing and/or stimulation device. As is shown by way of example in FIG. 8, the detection circuitry 902 may receive information from multiple physiologic and non-physiologic sensors.

The components, functionality, and structural configurations depicted herein are intended to provide an understanding of various features and combination of features that may be incorporated in a PIMD. It is understood that a wide variety of PIMDs and other implantable cardiac stimulation device configurations are contemplated, ranging from relatively sophisticated to relatively simple designs. As such, particular PIMD or cardiac stimulation device configurations may include particular features as described herein, while other such device configurations may exclude particular features described herein.

Figure 9:
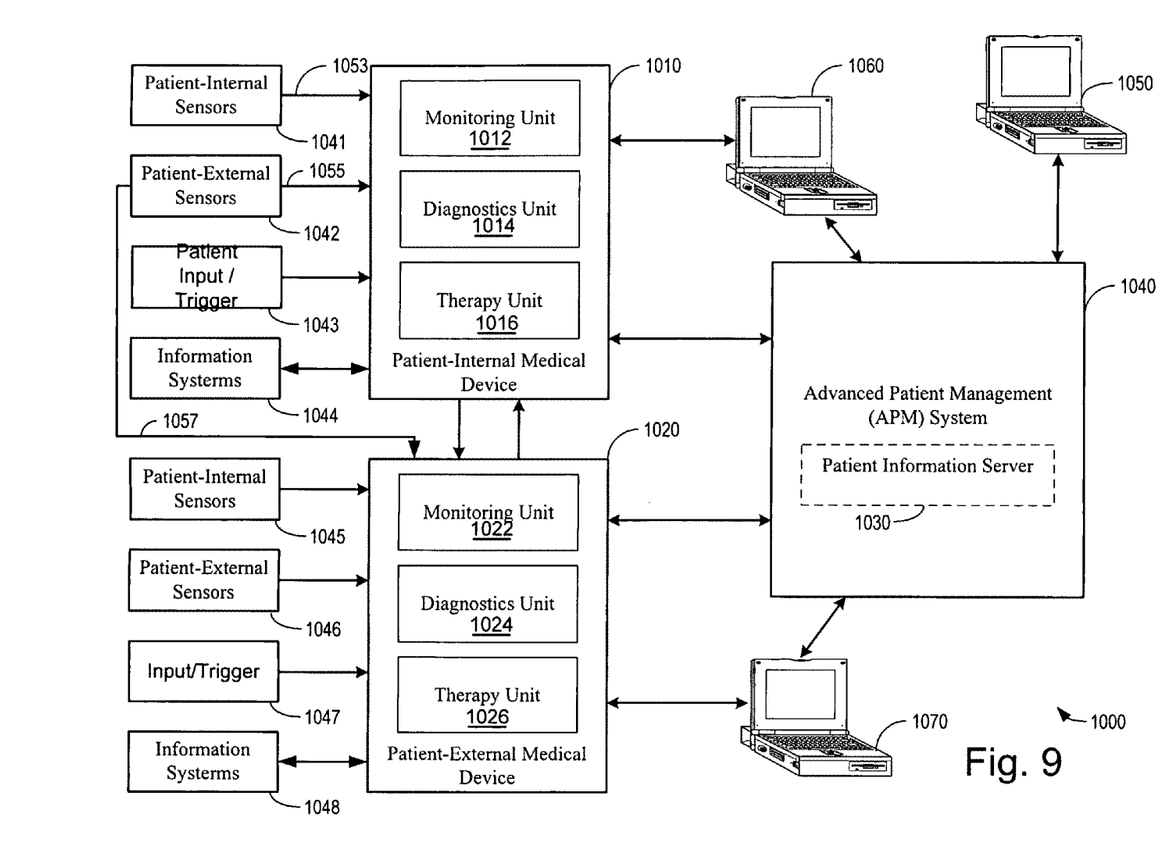
FIG. 9 is a block diagram of a medical system that may be used to implement system updating, coordinated patient monitoring, diagnosis, and/or therapy in accordance with embodiments of the present invention.

Referring now to FIG. 9, a PIMD of the present invention may be used within the structure of an advanced patient management (APM) system 1000. The advanced patient management system 1000 allows physicians to remotely and automatically monitor cardiac and respiratory functions, as well as other patient conditions. In one example, a PIMD implemented as a cardiac defibrillator may be equipped with various telecommunications and information technologies that enable real-time data collection, diagnosis, and treatment of the patient. Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

As is illustrated in FIG. 9, the medical system 1000 may be used to implement coordinated patient measuring and/or monitoring, diagnosis, and/or therapy in accordance with embodiments of the invention. The medical system 1000 may include, for example, one or more patient-internal medical devices 1010, such as a PIMD, and one or more patient-external medical devices 1020, such as a monitor or signal display device. Each of the patient-internal 1010 and patient-external 1020 medical devices may include one or more of a patient monitoring unit 1012, 1022, a diagnostics unit 1014, 1024, and/or a therapy unit 1016, 1026.

The patient-external medical device 1020 performs monitoring, and/or diagnosis and/or therapy functions external to the patient (i.e., not invasively implanted within the patient's body). The patient-external medical device 1020 may be positioned on the patient, near the patient, or in any location external to the patient.

The patient-internal and patient-external medical devices 1010, 1020 may be coupled to one or more sensors 1041, 1042, 1045, 1046, patient input/trigger devices 1043, 1047 and/or other information acquisition devices 1044, 1048. The sensors 1041, 1042, 1045, 1046, patient input/trigger devices 1043, 1047, and/or other information acquisition devices 1044, 1048 may be employed to detect conditions relevant to the monitoring, diagnostic, and/or therapeutic functions of the patient-internal and patient-external medical devices 1010, 1020.

The medical devices 1010, 1020 may each be coupled to one or more patient-internal sensors 1041, 1045 that are fully or partially implantable within the patient. The medical devices 1010, 1020 may also be coupled to patient-external sensors positioned on, near, or in a remote location with respect to the patient. The patient-internal and patient-external sensors are used to sense conditions, such as physiological or environmental conditions, that affect the patient.

The patient-internal sensors 1041 may be coupled to the patient-internal medical device 1010 through one or more internal leads 1053. Still referring to FIG. 9, one or more patient-internal sensors 1041 may be equipped with transceiver circuitry to support wireless communications between the one or more patient-internal sensors 1041 and the patient-internal medical device 1010 and/or the patient-external medical device 1020.

The patient-external sensors 1042 may be coupled to the patient-internal medical device 1010 and/or the patient-external medical device 1020 through one or more internal leads 1055 or through wireless connections. Patient-external sensors 1042 may communicate with the patient-internal medical device 1010 wirelessly. Patient-external sensors 1042 may be coupled to the patient-external medical device 1020 through one or more internal leads 1057 or through a wireless link.

In an embodiment of the present invention, the patient-external medical device 1020 includes a visual display configured to simultaneously display non-electrophysiological signals and ECG signals. For example, the display may present the information visually. The patient-external medical device 1020 may also, or alternately, provide signals to other components of the medical system 1000 for presentation to a clinician, whether local to the patient or remote to the patient.

Referring still to FIG. 9, the medical devices 1010, 1020 may be connected to one or more information acquisition devices 1044, 1048, such as a database that stores information useful in connection with the monitoring, diagnostic, or therapy functions of the medical devices 1010, 1020. For example, one or more of the medical devices 1010, 1020 may be coupled through a network to a patient information server 1030.

The input/trigger devices 1043, 1047 are used to allow the physician, clinician, and/or patient to manually trigger and/or transfer information to the medical devices 1010, 1020. The input/trigger devices 1043, 1047 may be particularly useful for inputting information concerning patient perceptions, such as a perceived cardiac event, how well the patient feels, and other information not automatically sensed or detected by the medical devices 1010, 1020. For example, the patient may trigger the input/trigger device 1043 upon perceiving a cardiac event. The trigger may then initiate the recording of cardiac signals and/or other sensor signals in the patient-internal device 1010. Later, a clinician may trigger the input/trigger device 1047, initiating the transfer of the recorded cardiac and/or other signals from the patient-internal device 1010 to the patient-external device 1020 for display and diagnosis.

In one embodiment, the patient-internal medical device 1010 and the patient-external medical device 1020 may communicate through a wireless link between the medical devices 1010, 1020. For example, the patient-internal and patient-external devices 1010, 1020 may be coupled through a short-range radio link, such as Bluetooth, IEEE 802.11, and/or a proprietary wireless protocol. The communications link may facilitate uni-directional or bi-directional communication between the patient-internal 1010 and patient-external 1020 medical devices. Data and/or control signals may be transmitted between the patient-internal 1010 and patient-external 1020 medical devices to coordinate the functions of the medical devices 1010, 1020.

In another embodiment, patient data may be downloaded from one or more of the medical devices periodically or on command, and stored at the patient information server 1030. The physician and/or the patient may communicate with the medical devices and the patient information server 1030, for example, to acquire patient data or to initiate, terminate or modify recording and/or therapy.

The data stored on the patient information server 1030 may be accessible by the patient and the patient's physician through one or more terminals 1050, e.g., remote computers located in the patient's home or the physician's office. The patient information server 1030 may be used to communicate to one or more of the patient-internal and patient-external medical devices 1010, 1020 to provide remote control of the monitoring, diagnosis, and/or therapy functions of the medical devices 1010, 1020.

In one embodiment, the patient's physician may access patient data transmitted from the medical devices 1010, 1020 to the patient information server 1030. After evaluation of the patient data, the patient's physician may communicate with one or more of the patient-internal or patient-external devices 1010, 1020 through an APM system 1040 to initiate, terminate, or modify the monitoring, diagnostic, and/or therapy functions of the patient-internal and/or patient-external medical systems 1010, 1020.

In another embodiment, the patient-internal and patient-external medical devices 1010, 1020 may not communicate directly, but may communicate indirectly through the APM system 1040. In this embodiment, the APM system 1040 may operate as an intermediary between two or more of the medical devices 1010, 1020. For example, data and/or control information may be transferred from one of the medical devices 1010, 1020 to the APM system 1040. The APM system 1040 may transfer the data and/or control information to another of the medical devices 1010, 1020.

In one embodiment, the APM system 1040 may communicate directly with the patient-internal and/or patient-external medical devices 1010, 1020. In another embodiment, the APM system 1040 may communicate with the patient-internal and/or patient-external medical devices 1010, 1020 through medical device programmers 1060, 1070 respectively associated with each medical device 1010, 1020. As was stated previously, the patient-internal medical device 1010 may take the form of an implantable PIMD.

A PIMD may operate in a batch mode or adaptively, allowing for on-line or off-line implementation. To save power, the system may include the option for a hierarchical decision-making routine that uses algorithms known in the art for identifying the presence of arrhythmias or noise in the collected signal and initiating the methods of the present invention. Various modifications and additions can be made to the preferred embodiments discussed hereinabove without departing from the scope of the present invention.

Accordingly, the scope of the present invention should not be limited by the particular embodiments described above, but should be defined only by the claims set forth below and equivalents thereof.

What is claimed is:

1. A method of delivering a subcutaneous defibrillation therapy from an extra-thoracic location, comprising:
   selecting at least a pair of subcutaneous electrodes from a plurality of subcutaneous electrodes positioned extra-thoracically relative to a patient's heart, the pair selected to provide an increased cardiac signal-to-noise ratio relative to other pairs of the plurality of subcutaneous electrodes;
   sensing a fibrillation event using the selected pair of subcutaneous electrodes of the plurality of subcutaneous electrodes;

determining a fibrillation cycle length associated with the sensed fibrillation event; and delivering, using one or more combinations of electrodes of the plurality of subcutaneous electrodes, a plurality of defibrillation pulses to treat the fibrillation event, wherein delivery of a latter pulse of the defibrillation pulses subsequent to a former pulse of the defibrillation pulses is separated in time by a first delay associated with the fibrillation cycle length.

2. The method of claim 1, further comprising delivering, using at least one of the combinations of electrodes, an additional defibrillation pulse following a second delay relative to delivery of the latter defibrillation pulse, the second delay associated with a percentage of the fibrillation cycle length.

3. The method of claim 2, wherein the first and second delays are associated with different percentages of the fibrillation cycle length.

4. The method of claim 1, wherein the former pulse is delivered from an electrode combination of the one or more electrode combinations different from that of the latter pulse.

5. The method of claim 1, wherein the fibrillation event is sensed by the selected subcutaneous electrode pair corresponding to a first electrode combination of the one or more electrode combinations and one or both of the former and latter pulses are delivered from a second electrode combination of the one or more electrode combinations.

6. The method of claim 1, wherein the first delay is greater than about 50 percent of the fibrillation cycle length.

7. The method of claim 1, wherein the first delay is greater than about 75 percent of the fibrillation cycle length.

8. The method of claim 1, wherein the first delay is about 75 to 100 percent of the fibrillation cycle length.

9. The method of claim 1, wherein the fibrillation cycle length is determined using a Fourier analysis of the fibrillation event or an auto-correlation analysis of the fibrillation event.

10. The method of claim 1, wherein the fibrillation cycle length is determined by counting signal features of the fibrillation event over a duration of time.

11. The method of claim 1, wherein the former and latter pulses are substantially similar in terms of one or more of amplitude, duration, and phase.

12. The method of claim 1, wherein the former and latter pulses are substantially different in terms of one or more of amplitude, duration, and phase.

13. The method of claim 1, wherein the former and latter pulses comprise monophasic waveforms, polyphasic waveforms, or a combination of monophasic and polyphasic waveforms.

14. A system for delivering a subcutaneous defibrillation therapy from an extra-thoracic location, comprising:

a housing configured for subcutaneous placement relative to a patient's heart;

detection circuitry provided in the housing, the detection circuitry configured to detect a fibrillation event;

energy delivery circuitry provided in the housing;

a plurality of combinations of electrodes configured for subcutaneous extra-thoracic placement relative to the patient's heart, the electrodes of each electrode combination coupled to the detection and energy delivery circuitry; and a controller provided in the housing and coupled to the detection and energy delivery circuitry, the controller configured to select a pair of subcutaneous electrodes from the plurality of electrode combinations based on an increased cardiac signal-to-noise ratio associated with the selected pair of subcutaneous electrodes relative to other pairs of the plurality of electrode combinations and to determine a fibrillation cycle length associated with the fibrillation event using the selected pair of subcutaneous electrodes, the controller coordinating delivery of a latter defibrillation pulse following a delay relative to delivery of a former defibrillation pulse, the delay defining a percentage of the fibrillation cycle length.

15. The system of claim 14, wherein the controller is configured to deliver an additional defibrillation pulse following a second delay relative to delivery of the latter defibrillation pulse, the second delay defining a percentage of the fibrillation cycle length.

16. The system of claim 14, wherein the selected electrode combination is used for detection of the fibrillation event and delivery of the former and latter defibrillation pulses.

17. The system of claim 14, wherein a first electrode combination of the plurality of electrode combinations is used for detection of the fibrillation event and a second electrode combination of the plurality of electrode combinations is used for delivery of at least one of the former and latter defibrillation pulses.

18. The system of claim 14, wherein a first electrode combination of the plurality of electrode combinations is used for delivery of the former defibrillation pulse and a second electrode combination of the plurality of electrode combinations is used for delivery of the latter defibrillation pulse.

19. The system of claim 14, wherein the delay is greater than about 50 percent of the fibrillation cycle length.

20. The system of claim 14, wherein the delay is greater than about 75 percent of the fibrillation cycle length.

21. The system of claim 14, wherein the delay is about 75 to 100 percent of the fibrillation cycle length.

22. The system of claim 14, wherein the controller is configured to determine the fibrillation cycle length using a Fourier analysis of the fibrillation event or an auto-correlation analysis of the fibrillation event.

23. The system of claim 14, wherein the controller is configured to determine the fibrillation cycle length by counting signal features of the fibrillation event over a duration of time.

24. The system of claim 14, wherein the former and latter defibrillation pulses are substantially similar in terms of one or more of amplitude, duration, and phase.

25. The system of claim 14, wherein the former and latter defibrillation pulses are substantially different in terms of one or more of amplitude, duration, and phase.

26. The system of claim 14, wherein the former and latter defibrillation pulses comprise monophasic waveforms, polyphasic waveforms, or a combination of monophasic and polyphasic waveforms.

27. A system for delivering a subcutaneous defibrillation therapy from an extra-thoracic location, comprising:

means for selecting a pair of subcutaneous electrodes from a plurality of subcutaneous extra-thoracic electrodes, the pair selected to provide an increased cardiac signal-to-noise ratio relative to other pairs of the plurality of subcutaneous extra-thoracic electrodes;

means for sensing a fibrillation event using the selected pair of subcutaneous extra-thoracic electrodes of the plurality of subcutaneous extra-thoracic electrodes;

means for determining a fibrillation cycle length associated with the fibrillation event;
means for delivering, using a first combination of electrodes of the plurality of subcutaneous extra-thoracic electrodes, a former defibrillation pulse to treat the fibrillation event; and
means for delivering, using the first combination or a second combination of electrodes of the plurality of subcutaneous extra-thoracic electrodes, a latter defibrillation pulse following a delay relative to delivery of the former defibrillation pulse to treat the fibrillation event, the delay associated with a percentage of the fibrillation cycle length.

* * * * *